US009034592B2

(12) United States Patent
Tamm et al.

(10) Patent No.: US 9,034,592 B2
(45) Date of Patent: May 19, 2015

(54) IMMUNOASSAY FOR QUANTIFICATION OF AN UNSTABLE ANTIGEN SELECTED FROM BNP AND PROBNP (75) Inventors: Natalia N. Tamm, Moscow (RU); Alexey G. Katrukha, Turku (FI); Vladimir L. Filatov, Moscow (RU); Olga V. Kolosova, Moscow (RU)

(73) Assignee: HYTEST LTD., Turku (FI)

( * ) Notice: Subject to any disclaimer, the term of this patent is extended or adjusted under 35 U.S.C. 154(b) by 101 days.

(21) Appl. No.: 13/600,873

(22) Filed: Aug. 31, 2012

(65) Prior Publication Data

US 2013/0071949 A1 Mar. 21, 2013

Related U.S. Application Data (62) Division of application No. 12/595,463, filed as application No. PCT/FI2008/050184 on Apr. 14, 2008.

(60) Provisional application No. 60/911,603, filed on Apr. 13, 2007.

(30) Foreign Application Priority Data

Apr. 13, 2007 (FI) ..................................... 20075251

(51) Int. Cl.
*C07K 16/26* (2006.01)
*G01N 33/68* (2006.01)
*G01N 33/74* (2006.01)

(52) U.S. Cl.
CPC ............. *C07K 16/26* (2013.01); *C07K 2317/32* (2013.01); *G01N 33/74* (2013.01); *G01N 33/6887* (2013.01); *G01N 33/6893* (2013.01); *C07K 2317/34* (2013.01)

(58) Field of Classification Search
None
See application file for complete search history.

(56) References Cited

U.S. PATENT DOCUMENTS

| 5,583,003 | A | * | 12/1996 | Hillyard et al. | ............... | 435/7.25 |
| 5,985,579 | A | * | 11/1999 | Buechler et al. | ............... | 435/7.1 |
| 7,731,965 | B2 | | 6/2010 | Shih et al. | | |
| 2003/0219734 | A1 | | 11/2003 | Buechler | | |
| 2006/0183154 | A1 | * | 8/2006 | Shih et al. | ....................... | 435/7.1 |
| 2008/0248491 | A1 | | 10/2008 | Wu et al. | | |

FOREIGN PATENT DOCUMENTS

| EP | 1378242 A1 | 1/2004 |
| WO | 2004/046733 A1 | 6/2004 |

OTHER PUBLICATIONS

Bayer Diagnostics, "BNP", 2002, retrieved from http://www.medical.siemens.com/siemens/en_GLOBAL/gg_diag_FBAs/files/immundiagnostik_de_pdf/centaur_de_pdf/bnp_engl.pdf on Apr. 12, 2013, three pages.*
Tamm et al. "Measurement of B-type natriuretic peptide by two assays utilizing antibodies with different epitope specificity" Clin Biochem. Feb. 2011;44(2-3):257-9.*
Colman et al. "Effects of Amino Acid Sequence Changes on Antibody-Antigen Interactions", Research in Immunology, 1994; 145(1): 33-36.*
Abaza et al. "Effects of amino acid substitutions outside an antigenic site on protein binding to monoclonal antibodies of predetermined specificity obtained by peptide immunization: demonstration with region 94-100 (antigenic site 3) of myoglobin" Journal of Protein Chemistry, vol. 11, No. 5, 1992, pp. 433-444.*
Harlow, E. and Lane, D., Antibodies: A Laboratory Manual (1988) Cold Spring Harbor Laboratory Press, Cold Spring Harbor, NY, pp. 23-26.*
Lederman et al. "A single amino acid substitution in a common African allele of the CD4 molecule ablates binding of the monoclonal antibody, OKT4" Mol Immunol. Nov. 1991;28(11):1171-81.*
HyTest Web Store, "Monoclonal mouse anti-immune complex (24C5-BNP/proBNP) Cat.#4BFab5", retrieved from https://shop.hytest.fi/product/immune-complex-24c5-bnpprobnp-antibody on Mar. 21, 2015, three pages.*
HyTest Web Store, "Monoclonal mouse anti-human brain natriuretic peptide (BNP) Cat.# 4BNP2", retrieved from https://shop.hytest.fi/product/bnp-human-antibody on Mar. 21, 2015, four pages.*
Diamond et al. (1985) Site of Binding of IgG2b and IgG2a by Mouse Macrophage FcReceptors by Using Cyanogen Bromide Fragments, J. Immunol., 134(2):1080-1083.
HyTest Ltd (DataSheet for Catalog # 4BFab5, Product Name "Monoclonal mouse anti-immune complex (24C5-BNP/proBNP)", retrieved from http://www.hytest.fi/print/product/immune-complex-24c5-bnpprobnp-antibody on Nov. 15, 2012, 2 pages).
BioAtla, "Antibody Structure", retrieved from http://www.bioatla.com/antibody-structure/ on Nov. 16, 2012 (4 pages).
HyTest News ("ProBNP and proBNP derived peptides BNP and NT-proBNP", retrieved from http://www.hytest.fi/data_sheets/newsletters/ProBNP%20and%20Derivatives%20Newsletter.pdf (Jun. 2007) on Nov. 16, 2012, (12 pages).
Harlow et al. (1988) Antibodies: A Laboratory Manual, Cold Spring Harbor Laboratory Press, Cold Spring Harbor, NY, pp. 23-26 (12 pages with bibliog).

(Continued)

*Primary Examiner* — Christine Foster
(74) *Attorney, Agent, or Firm* — Ann-Louise Kerner; DLA Piper LLP (US)

(57) ABSTRACT

The present invention relates to an immunoassay for detection of BNP, proBNP and fragments thereof. Essentially the assay comprises: a) contacting the antigen with a first antibody specific to a fragment corresponding to amino acids 11-22 of BNP, or to a part of this peptide comprising at least three amino acids of said sequence, to obtain a first order immune complex. b) contacting the first order immune complex obtained at step (a) with a second antibody recognizing said first order immune complex, to obtain a second order immune complex, wherein said antibody is unable to recognize free BNP, proBNP or free first antibody; c) Detecting the second order immune complex.

7 Claims, 6 Drawing Sheets (56) References Cited

OTHER PUBLICATIONS

Hammerer-Lercher et al., "Natriuretic Peptides as Markers of Mild Forms of Left Ventricular Dysfunction: Effects of Assays on Diagnostic Performance of Markers," Clinical Chemistry, 50(7):1174-1183 (2004).
Seferian et al., "The Brain Natriuretic Peptide (BNP) Precursor is the Major Immunoreactive Form of BNP in Patients with Heart Failure," Clinical Chemistry, 53(5):866-873 (2007).
Nagata et al., "A New Type Sandwich Immunoassay for Microcystin: Production of Monoclonal Antibodies specific to the Immune Complex Formed by Microcystin and an Anti-Microcystin Monoclonal Antibody," Natural Toxins, 7:49-55 (1999).
Volland et al., "Recent Developments for SPIE-IA, a New Sandwich Immunoassay Format for Very Small Molecules," J. Pharm. Biomed. Anal., 34:737-752 (2004).
Towbin et al., "Sandwich Immunoassay for the Hapten Angiotensin II," J. Immunol. Methods, 181:167-176 (1995).
Self et al., "High-Performance Assays of Small Molecules; Enhanced Sensitivity, rapidity, and Convenience Demonstrated with a Noncompetitive Immunometric Anti-Immune Complex Assay System for Digoxin," Clinical Chemistry, 40(11):2035-2041 (1994).
Apple et al., "Quality Specifications for B-Type Natriuretic Peptide Assays," Clinical Chemistry, 51(3):486-493 (2005).
Written Opinion and International Search Report, dated Aug. 26, 2008, for PCT/FI2008/050184, 10 Pages.
Morrison et al. (2002) "Utility of a Rapid B-Natriuretic Peptide Assay in Differentiating Congestive Heart Failure From Lung Disease in Patients Presenting With Dyspnea," J. Am. Coll. Cardiol. 39(2):202-209.
Rawlins et al. (2005) "Performance Characteristics of Four Automated Natriuretic Peptide Assays," Am. J. Clin. Pathol. 123:439-445.
Sykes et al. (2005) "Analytical Relationships Among Biosite, Bayer, and Roche Methods for BNP and NT-proBNP, A Preliminary Study," Am. J. Clin. Pathol. 123:584-590.
Wians, Jr. et al. (2005) "Evaluation of the Analytical Performance Characteristics of the Bayer ACS:180® B-Type Natriuretic Peptide (BNP) Assay," Clinica Chimica Acta 353:147-155.
Wu et al. (2004) "Analytical and Clinical Evaluation of the Bayer ADVIA Centaur Automated B-Type Natriuretic Peptide Assay in Patients With Heart Failure: A Multisite Study," Clin. Chem. 50(5):867-873.
Belenky et al. (2004) "The effect of class-specific protease inhibitors on the stabilization of B-type natriuretic peptide in human plasma," Clinica Chimica Acta 340:163-172.
Al-Mahdili et al. (2010) "High-dose hook effect in six automated human chorionic gonadotrophin assays," Annals Clin. Biochem. 47:383-385.
Anand et al. (2003) Changes in brain natriuretic peptide and norepinephrine over time and mortality and morbidity in the valsartan heart failure trial (Val-HeFT), Circulation 107:1278-1283.
Anido (1984) "Seven Ferritin Kits Compared with Respect to the Hook Effect" Chem. 30(3):500.
Apple et al. (2007) "National Academy of Clinical Biochemistry and IFCC Committee for Standardization of Markers of Cardiac Damage Laboratory Medicine Practice Guidelines: Analytical issues for biomarkers of heart failure," Circulation 116:e95-e98.
Beilby (2008) "Guideline Reviews: National Academy of Clinical Biochemistry (NACB) laboratory medicine guidelines on the clinical utilization and analytical issues for cardiac biomarker testing in heart failure," Clin. Biochem. Rev. 29:107-111.
Brenden et al. (2006) "Gray zone BNP levels in heart failure patients in the emergency department: Results from the Rapid Emergency Department Heart Failure Outpatient Trial (REDHOT) multicenter study," Am. Heart J. 151:1006-1011.
Charrie et al. (1995) "Hook effect in immunometric assays for prostate-specific antigen," Clin. Chem. 41(3):480-481.
Cole et al. (1993) "Cost-effective method for detection of 'hook effect' in tumor marker immunometric assays," Clin. Chem. 39(4):695-696.
Desilva et al. (2003) "Recommendations for the Bioanalytical Method Validation of Ligand-binding Assays to Support Pharmacokinetic Assessments of Macromolecules," Pharma. Res. 20(11):1885-1900.
Fernando et al. (1992) "Studies of the 'hook' effect in the one-step sandwich immunoassay," J. Immunolog. Meth. 151:47-66.
Frieze et al. (2002) "'Hook effect' in prolactinomas: case report and review of literature," Endocr. Pract. 8(4):296-303.
Grassi et al. (1996) "Two different approaches for developing immunometric assays of haptens," Clin. Chem. 42 (9):1532-1536.
Inaba et al. (2009) "Anti-metatype peptides, a molecular tool with high sensitivity and specificity to monitor small ligands," Anal. Biochem. 388:63-70.
Katrukha et al. (2005) "New sensitive Sandwich time-resolved immunofluorometric assay for quantification of BNP in human blood," Clin. Chem. 51(6)(Suppl.):A26.
Katrukha et al. (2005) "New sensitive Sandwich time-resolved immunofluorometric assay for quantification of BNP in human blood," AACC Poster A-82, Orlando FL, 1 page).
Kenny et al. (1993) "Hydrolysis of human and pig brain natriuretic peptides, urodilatin, C-type natriuretic peptide and some C-receptor ligands by endopeptidase-24.11," Biochem. J. 291:83-88.
Kobayashi et al. (2000) "Monoclonal antibodies generated against an affinity-labeled immune complex of an anti-bile acid metabolite antibody: an approach to noncompetitive hapten immunoassays based on anti-idiotype or antimetatype antibodies," J. Immunolog. Meth. 245:95-108.
Hartmann et al. (2004) Prognostic Impact of Plasma N-Terminal Pro-Brain Natriuretic Peptide in Severe Chronic Congestive Heart Failure—A Substudy of the Carvedilol Prospective Randomized Cumulative Survival (COPERNICUS) Trial, Circulation, 110:1780-1786.
Maisel et al. (2002) "Rapid measurement of B-type natriuretic peptide in the emergency diagnosis of heart failure," N. Engl. J. Med. 347(3):161-167, 1126.
Maisel et al. (2008) "Timing of immunoreactive b-type natriuretic peptide levels and treatment delay in acute decompensated heart failure," J. Amer. Coll. Cardiol., 52(7):534-540.
Norman et al. (1981) "Degradation of brain natriuretic peptide by neutral endopeptidase: species specific sites of proteolysis determined by mass spectrometry," Biochem. Biophys. Res. Comm. 175(1):22-30.
Omland et al. (2009), "Natriuretic Peptides: Physiologic and Analytic Considerations," Heart Failure Clin. 5:471-487.
Porstmann et al. (1992) "Enzyme immunoassay techniques: An overview," J. Immunolog. Meth., 150:5-21.
Revenant et al. (1982), Serum Ferritin Determination by Enzyme Immunoassay: Importance of Sample dilution (the "Hook Effect"), Clin. Chem., 28(1):253.
Roberts et al. (2001) "Evaluation of nine automated high-sensitivity C-reactive protein methods: implications for clinical and epidemiological applications (Part 2)" Clin. Chem. 47(3):418-425.
Schofl et al. (2002) "Falsely low serum prolactin in two cases of invasive macroprolactinoma," Pituitary 5:261-265.
Tamm et al. (2007) New type of immunoassay for quantification of brain natriuretic peptide (BNP) and its precursor—proform of brain natriuretic peptide (ProBNP) in human blood (AACC Poster and Abstract), 2 pages.
Thygesen et al. (2012) "Recommendations for the use of natriuretic peptides in acute cardiac care" Euro. Heart J. 33:2001-2006c.
Valentin et al. (2011) "Validation of immunoassay for protein biomarkers: bioanalytical study plan implementation to support preclinical and clinical studies" J. Pharma. Biomed. Anal. 55:869-877.
Watanabe et al. (1997) "Comparison of the hydrolysis of the three types of natriuretic peptides by human kidney neutral endopeptidase 24.11" Biochem. Mol. Med. 61:47-51.
FDA Decision Summary Triage, 510k No. k040437, 6 pages.
FDA Decision Summary Triage BNP Test, 510k No. k052789, 6 pages.
FDA Decision Summary i-STAT, 510k No. k053597, 10 pages.
FDA Decision Summary (2003) Bayer ADVIA Centaur, k031038, 8 pages.

(56) References Cited

OTHER PUBLICATIONS

FDA Decision Summary (2004) Bayer ACS 180 and ADVIA Centaur, k040425, 8 pages.
FDA Decision Summary Axis Shield, 510k No. k033606, 8 pages.
FDA—Class II Special Control Guidance Document for B-Type Natriuretic Peptide Premarket Notifications; Final Guidance for Industry and FDA Reviewers (2000) 5 pages.
FDA—Guidance Document for the Submission of Tumor Associated Antigen Premarket Notifications, [510(k)], to FDA (1996) 23 pages.
The Immunoassay Handbook (2nd Ed.), David Wild, Ed., (2001) pp. 10, 12, 14, and 86-87.
The Immunoassay Handbook, David Wild, Ed., (2005) p. 626.
The Immunoassay Handbook (2013) Elsevier Ltd., p. 689.
Christopoulos et al. (1996) Immunoassay, Academic Press, Inc., pp. 230-231.
Towbin et al. (1995) "Sandwich immunoassay for the hapten angiotensin II: A novel assay principle based on antibodies against immune complexes" J. Immunol. Meth. 181:167-176.

* cited by examiner

IMMUNOASSAY FOR QUANTIFICATION OF AN UNSTABLE ANTIGEN SELECTED FROM BNP AND PROBNP

CROSS-REFERENCE TO RELATED APPLICATIONS

This application is a divisional of and claims the benefit of and priority to U.S. patent application Ser. No. 12/595,463, entitled "IMMUNOASSAY FOR QUANTIFICATION OF AN UNSTABLE ANTIGEN SELECTED FROM BNP AND proBNP," filed on Oct. 9, 2009, which is a U.S. national phase application of International Patent Application No. PCT/FI2008/050184 filed on Apr. 14, 2008, which claims priority under 35 U.S.C. 119(e) to U.S. Provisional Application No. 60/911,603, filed on Apr. 13, 2007, and under 35 U.S.C. 119(a) to Patent Application No. 20075251 filed in Finland on Apr. 13, 2007, all of which are hereby expressly incorporated by reference into the present application.

FIELD OF THE INVENTION

The present invention relates to immunoassays, and provides an immunoassay method for detection of unstable antigens. The method is specifically suitable for detection of BNP, proBNP, and fragments thereof.

BACKGROUND OF THE INVENTION

BNP and proBNP are reliable markers of heart failure (HF) widely used in clinical practice. Several types of sandwich immunoassays (conventional assays) utilizing two mono- or polyclonal antibodies, specific to different epitopes of BNP or BNP-fragment of proBNP molecule are described in literature.

BNP molecule is known as an extremely unstable molecule rapidly losing its immunological activity in water solutions. This loss of activity is usually associated with proteolytic degradation of the peptide. Sandwich immunoassays commonly used for qualitative or quantitative antigen immunodetection utilize two or more antibodies specific to two or more different epitopes. The longer is the distance between the epitopes, the higher is the probability that sites of proteolysis would be located between the epitopes of the antibodies, thus increasing the sensitivity of the assay to proteolytic degradation of the antigen. And vice versa, the closer are the epitopes to each other, the smaller is the probability of the proteolytic cleavage of the molecule between the epitopes.

Immunoassay methods for very small molecules have been described, including the application of so called antimetatype antibodies. Such methods are disclosed, e.g. for detecting digoxin (Self et al., 1994, Clin. Chem. 40:2035-2041), and angiotensin II (Towbin et al., 1995, J. Immunol. Meth. 181:167-176).

However, it is not an easy task to apply this type of method to different analytes, since very specific monoclonal antibodies are required in such a method.

DESCRIPTION OF THE INVENTION

Here we are describing an immunoassay for quantification of BNP and proBNP in human blood. We have named the assay as "unequal sandwich". This assay is applicable to immunodetection of all unstable antigens.

Figure 1:
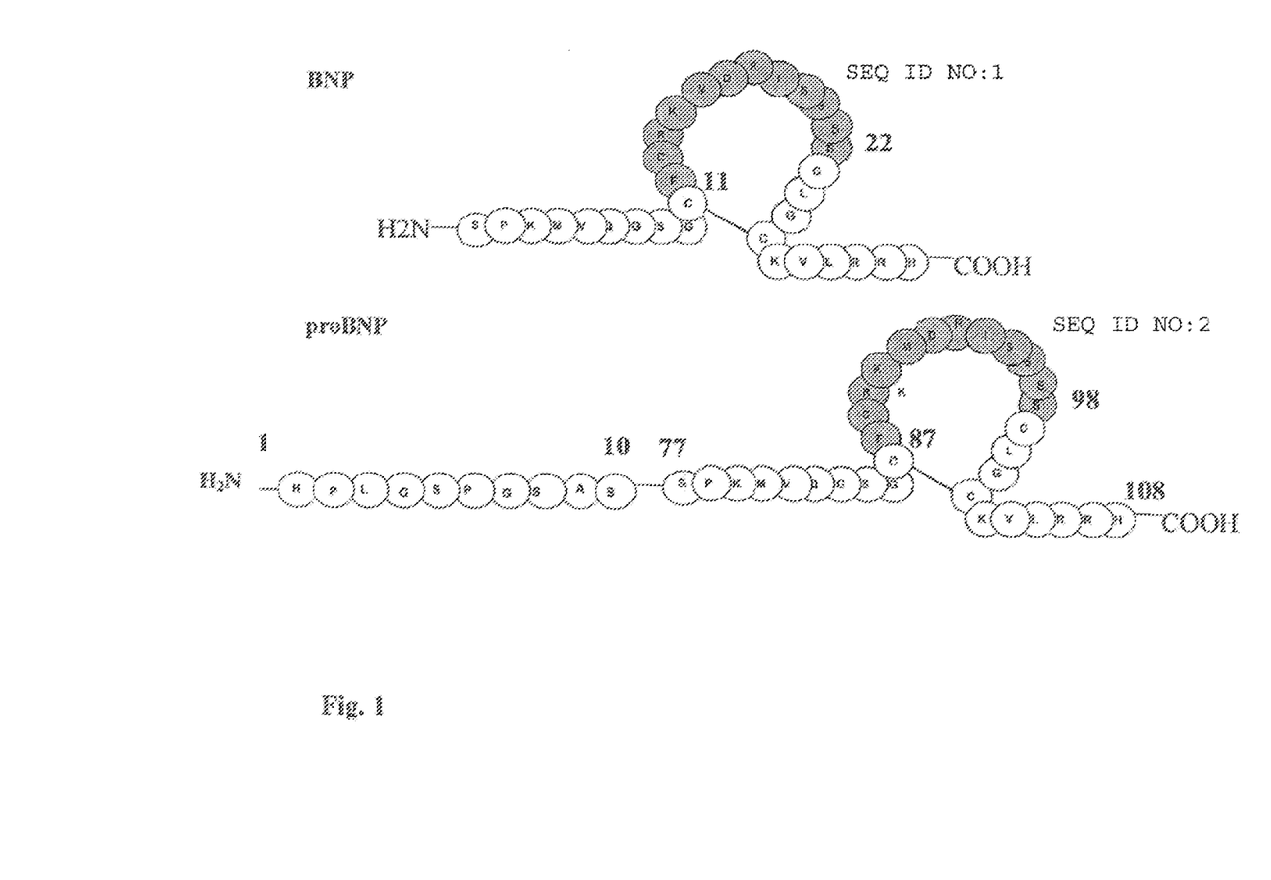
FIG. 1. BNP and pro BNP structures and epitope specificity of MAb 24C5.

The immunoassay described in the present application utilizes two different monoclonal antibodies. In detection of BNP or proBNP the first monoclonal antibody (MAb 24C5) is specific to the region (or a part of this region) comprising amino acid residues 11-22 ($_{11}$FGRKMDRISSSS$_{22}$) (amino acids 11-22 of SEQ ID NO:1) of BNP (which correspond to amino acid residues 87-98 of proBNP) (FIG. 1). The second antibody (namely MAbs Ab-BNP2 and Ab-BNP4), labeled with a signal-producing component, recognizes an immune complex of the first antibody with antigen (BNP, proBNP, or a fragment thereof comprising amino acid residues $_{11}$FGRKMDRISSSS$_{22}$ (amino acids 11-22 of SEQ ID NO:1) or a part of this sequence comprising at least three amino acid residues of said sequence). Second antibody does not recognize (or recognizes with very low affinity—10-fold or less) either free antigen or its fragments, or free MAb 24C5. Thus the primary immune complex comprising MAb 24C5 and BNP (or proBNP, or a fragment thereof) serves as an antigen for the second antibody (MAbs Ab-BNP2 and Ab-BNP4).

Consequently, the general object of the present invention is an immunoassay method for detecting an unstable antigen in a sample, comprising:
(a) contacting an antigen of interest with a first antibody specific to a first epitope of the antigen molecule, to obtain a first order immune complex,
(b) contacting the first order immune complex obtained at step (a) with a second antibody, which recognizes said first order immune complex and is specific to a second epitope formed by the antigen of interest and the first antibody, to obtain a second order immune complex, wherein said second antibody is unable to recognize free antigen or a fragment thereof or free first antibody, or recognizes them with significantly lower affinity—10-fold or less—than they recognize the first order immune complex, and
(c) detecting the second order immune complex formation.

A specific object of the invention is an immunoassay method for detecting an antigen selected from the group consisting of BNP, proBNP, and a fragment thereof in a sample, comprising:
(a) contacting the antigen with a first antibody specific to the fragment $_{11}$FGRKMDRISSSS$_{22}$ (amino acids 11-22 of SEQ ID NO:1) of BNP molecule or to a part of this peptide comprising at least three amino acid residues of said sequence, to obtain a first order immune complex,
(b) contacting the first order immune complex obtained at step (a) with a second antibody recognizing said first order immune complex, to obtain a second order immune complex, wherein said second antibody is unable to recognize free BNP, proBNP or a fragment thereof or free first antibody, or recognizes them with significantly lower affinity—10-fold or less—than it recognizes the first order immune complex, and
(c) detecting the second order immune complex formation.

We have succeeded in producing specific monoclonal antibodies applicable in the method of the invention. These antibodies are specific objects of the present invention.

Unequal sandwich described herein demonstrates extraordinary insusceptibility to proteolytic degradation of the antigen in comparison with the assays utilizing antibodies specific to distantly located epitopes.

Also such approach could be useful in the cases where the assay is developed for immunodetection of the antigen which is similar to one or more other antigens; has numerous different epitopes on its surface, but has only one (or more, but very limited number) of unique epitopes, that distinguishes that particular antigen from all others.

BRIEF DESCRIPTION OF THE DRAWINGS

MAb 24C5 recognizes fragment of BNP molecule comprising amino acid residues 11-22 of SEQ ID NO:1 and proBNP fragment consisting of amino acid residues 87-98 of SEQ ID NO:2 (marked by dark).

Eu-labelled MAbs 24C5, Ab-BNP2, Ab-BNP4 (200 ng/well) were incubated in plates coated with:
A. BNP 50 ng/well
B. proBNP 100 ng/well
C. polyclonal anti-BNP antibodies (2 .mu.g/well) preincubated with BNP (0.5 ng/well)

Three-step assay protocol:
First step: plates were precoated with capture MAb 24C5
Second step: After washing the plates were incubated with antigen (BNP or Peptide 11-22);
Third step: After washing the plates were incubated with detection (Eu.sup.3+ labeled) antibodies (Ab-BNP2, Ab-BNP4 or 57H3).
After washing enhancement solution was added and the signal was measured.

Three-step assay protocol:
First step: Plates were precoated with capture MAb 24C5
Second step: After washing the plates were incubated with proBNP (5 ng/ml)
Third step: After washing the plates were incubated with detection antibodies (Ab-BNP2, Ab-BNP4 or 57H3).
After washing enhancement solution was added and the signal was measured.

Synthetic BNP was spiked into pooled normal human plasma (2 ng/ml), incubated at +4.degree. C. for different periods of time. Immunological activity was tested in three different assays—one conventional and two unequal sandwiches.

EXPERIMENTAL

Remarks: Antibodies labeled with stable Eu-chelate were used in all experiments as detection antibodies. The monoclonal antibodies 24C5, Ab-BNP2, Ab-BNP4, 57H3 and 50E1 used in the experiments are available from Hytest Ltd, Turku, Finland.

Example 1

Figure 2A:
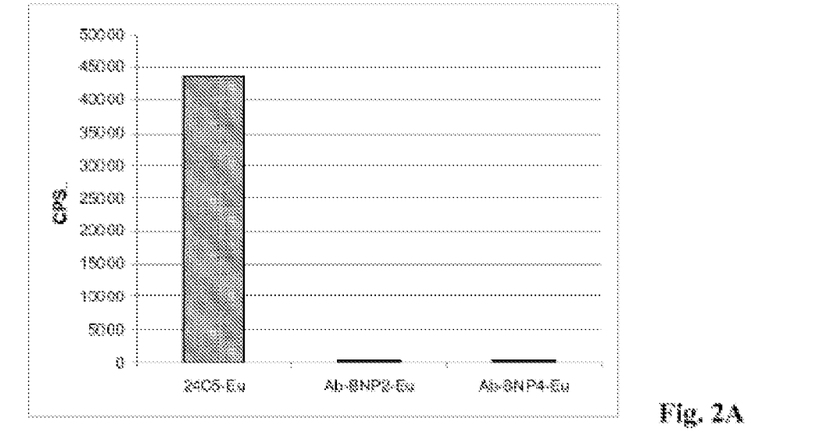
FIGS. 2A, 2B and 2C. Antibodies Ab-BNP2 and Ab-BNP4 do not recognize either BNP or proBNP that are not complexed with MAb 24C5.
Figure 2B:
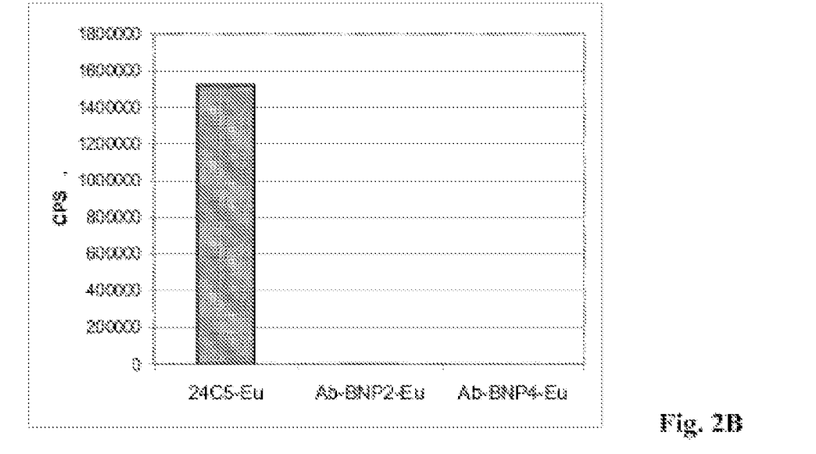
Figure 2C:
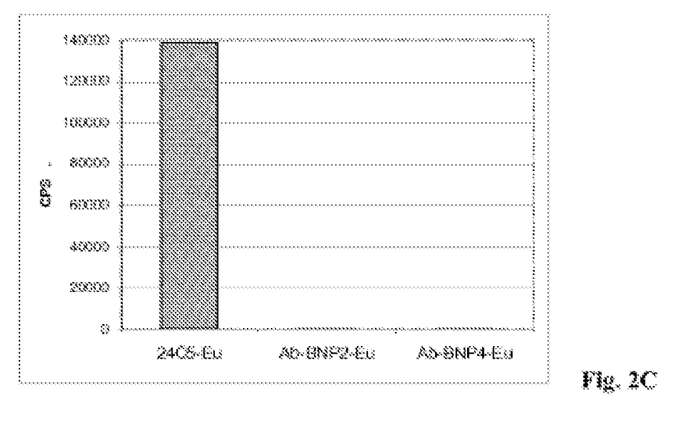

Antibodies Ab-BNP2 and Ab-BNP4 do not Recognize Either BNP or proBNP that are not Complexed with MAb 24C5 (FIG. 2)

In the experiment presented in the FIG. 2A and FIG. 2B antigens (BNP and proBNP, respectively) were used for plate coating and Eu-labeled antibodies were tested with the antigen in direct immunoassay. Antibody 24C5 recognizes both forms of the antigen, whereas MAbs Ab-BNP2 and Ab-BNP4 give no response (signal comparable with background) with any of the two antigens.

In the experiment presented in FIG. 2C the plates were coated with polyclonal antibodies specific to different epitopes on BNP molecule. On the second step the plates were incubated with BNP and then with Eu-labeled antibodies. Such approach helps to obtain variable orientation of the antigen against plate surface, insuring that orientation of the molecule on the plate surface does not have influence on the experimental results. In this experiment the same results as described above were obtained: MAbs Ab-BNP2 and Ab-BNP4 were not able to recognize the antigen, which is not complexed with MAb 24C5.

Example 2

Figure 3:
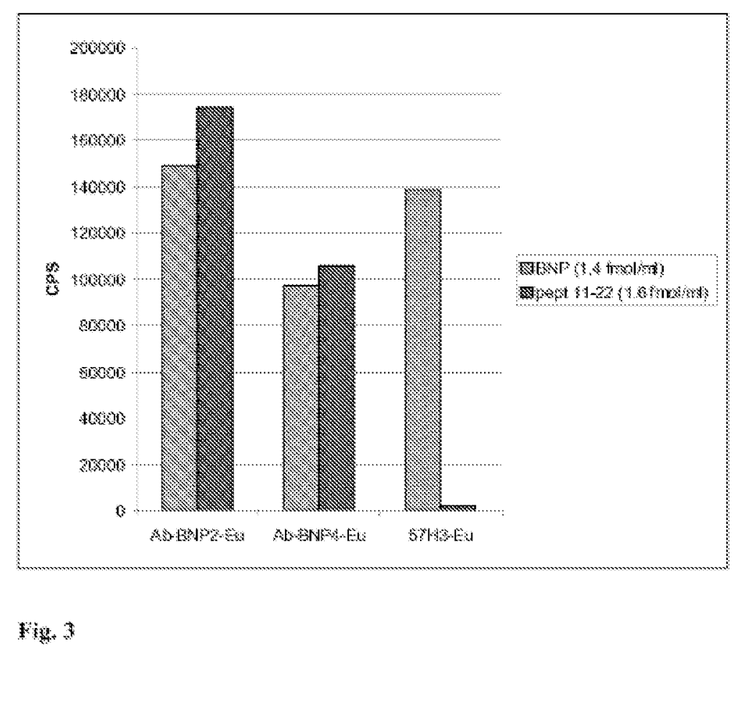
FIG. 3. Antibodies Ab-BNP2 and Ab-BNP4 can recognize immune complex of BNP (or Peptide 11-22) with MAb 24C5

Antibodies Ab-BNP2 and Ab-BNP4 can Recognize BNP and Peptide 11-22, that are Forming Immune Complex with MAb 24C5 (FIG. 3)

MAb 24C5 is specific to the fragment 11-22 of BNP molecule or to the corresponding region 87-98 of proBNP. To demonstrate that immune complex 24C5-BNP and 24C5-peptide 11-22 could be recognized by MAbs Ab-BNP2 and Ab-BNP4 we used MAb 24C5 for plate coating, then incubated the plates with BNP or synthetic peptide corresponding to amino acids 11-22 of BNP sequence (Peptide 11-22). After the immune complex between MAb 24C5 and antigens was formed, the plates were incubated with Eu-labeled antibodies Ab-BNP2, Ab-BNP4 and 57H3, specific to the region 26-32 of the BNP molecule.

Unequal sandwich recognizes BNP and the peptide almost with the same efficiency. Assay utilizing antibodies 24C5 (coating)—57H3-Eu does not recognize Peptide 11-22 (signal comparable with the background).

Example 3

Figure 4:
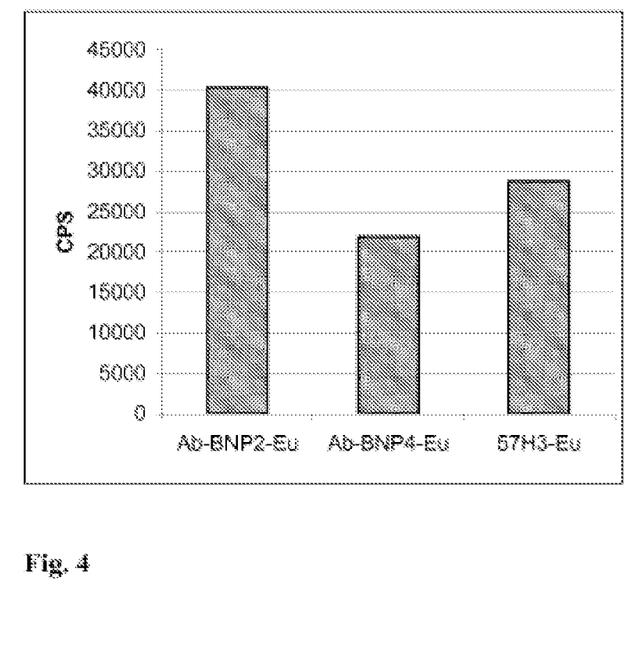
FIG. 4. Antibodies Ab-BNP2 and Ab-BNP4 can recognize proBNP, which forms immune complex with MAb 24C5

Antibodies Ab-BNP2 and Ab-BNP4 can Recognize proBNP, which Forms Immune Complex with MAb 24C5 (FIG. 4)

Unequal sandwich recognizes proBNP with the same efficiency as a conventional assay. We used MAb 24C5 for plate coating and then incubated plates firstly with recombinant proBNP (5 ng/ml) and secondly with Eu-labeled antibodies Ab-BNP2, Ab-BNP4 and 57H3 specific to the region 26-32 of BNP molecule. The signals obtained in the unequal sandwich and conventional immunoassays are comparable. We concluded that new assays could be used for quantitative immuno detection of proBNP.

Example 4

Figure 5:
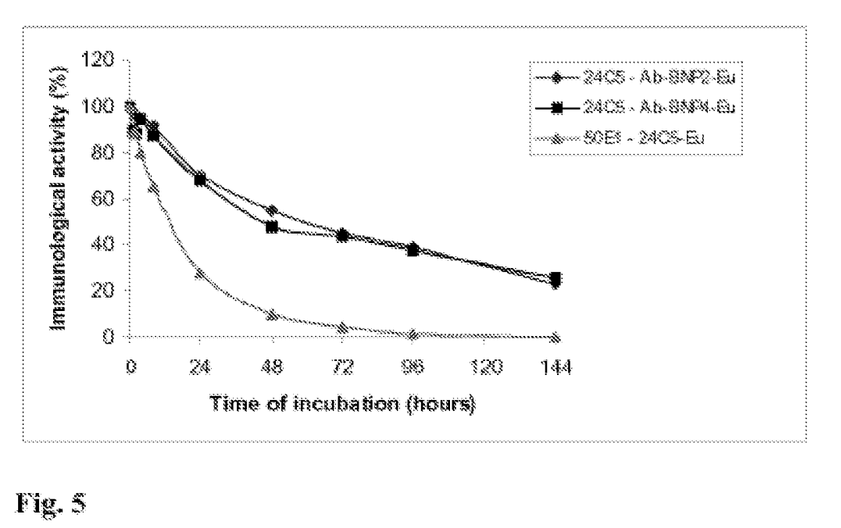
FIG. 5. Stability of BNP in normal human plasma.

Apparent Stability of the Antigen (FIG. 5)

Synthetic BNP (Bachem) was spiked into pooled normal human plasma (2 ng/ml), incubated at +4.degree. C. for different periods of time and the immunological activity was tested in three different assays—one conventional and two unequal sandwiches.

Apparent stability of the antigen, being determined in unequal sandwiches, described here is significantly higher in comparison with the stability determined by the conventional BNP assays utilizing two MAbs specific to different parts of BNP molecule. As an example of conventional assay we used assay, utilizing MAb 50E1 specific to the region 26-32 of BNP molecule and MAb 24C5 specific to the region 11-22 of BNP molecule. About 70% of immunological activity was observed after 24 hours of incubation at +4.degree. C. (69.8% and 68% for assays utilizing Ab-BNP2 and Ab-BNP4, respectively) in the case the unequal sandwich was used to determine the immunoreactivity, and only 28% in the case of conventional assay. Six days after the beginning of incubation no immunoreactivity was observed in case of conventional assays, whereas about ¼ of initial immunoreactivity was observed in the case of unequal sandwiches.

Example 5

Figure 6:
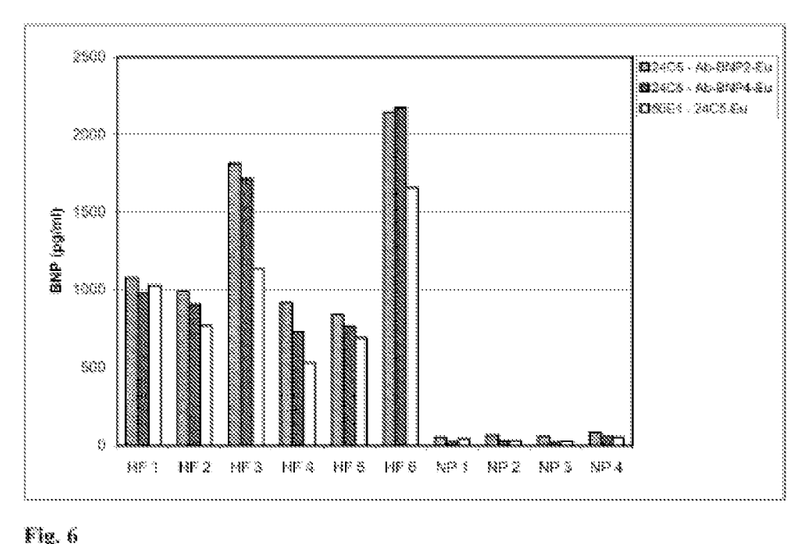
FIG. 6. BNP/proBNP measurements in blood of patients with HF and healthy donors. Plasma samples of 6 patients with heart failure (HF 1-HF 6) and plasma samples of healthy donors (NP1-NP4) were tested in three assays. Synthetic BNP (Bachem) was used as a calibrator in all assays.

BNP/proBNP Measurements in Blood of Heart Failure Patients (HF Patients) and Blood of Healthy Donors (FIG. 6)

Unequal sandwich, as well as conventional BNP assays are able to detect in human blood both forms of the antigen displaying "BNP immunoreactivity"—i.e. BNP and proBNP. Blood samples from several HF patients and healthy donors were tested in three assays—one conventional, utilizing capture MAb 50E1, specific to the fragment 26-32 of BNP molecule and detection MAb 24C5-Eu and two unequal sandwiches. All assays were calibrated using synthetic BNP. As it follows from FIG. 6, the results of testing in three assays are very similar. In some samples results of testing in conventional assay are lower than in unequal sandwiches. This observation can be explained by the fact that in such samples BNP is partially degraded, but because of the fact that antigen displays better apparent stability in unequal sandwiches the antigen values determined by these assays are higher than in a conventional assay.

Example 6

Figure 7A:
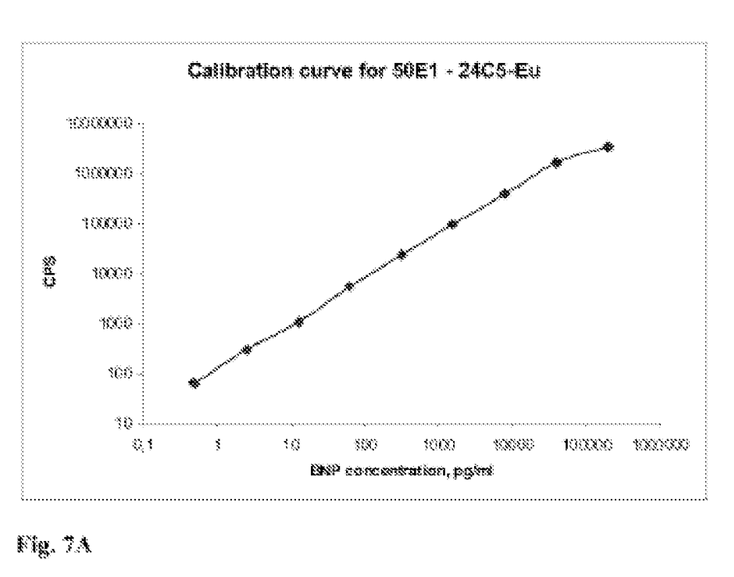
FIGS. 7A, 7B and 7C. Calibration curves for two unequal sandwiches (24C5-Ab-BNP2, 24C5-Ab-BNP4) and one conventional assay (50E1-24C5-Eu). Antigen: synthetic BNP (Bachem).
Figure 7B:
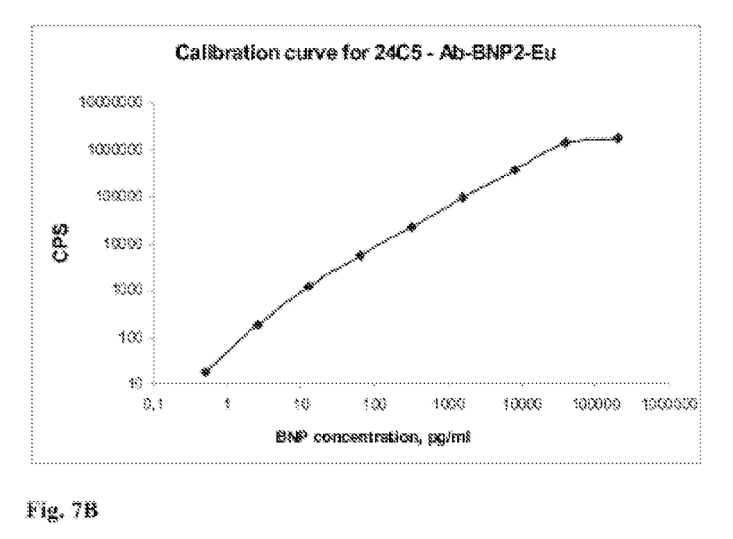
Figure 7C:
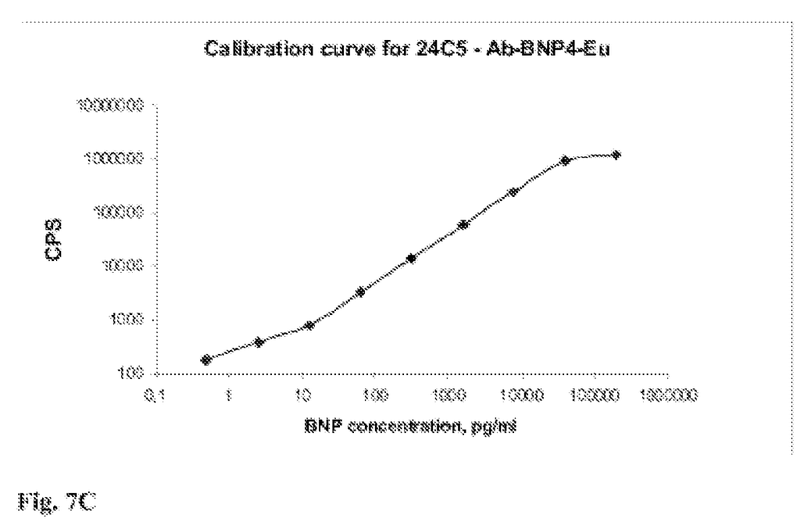

Calibration Curves (FIG. 7)

Calibration curves for two unequal sandwiches and one conventional assay with synthetic BNP used as an antigen are presented in FIGS. 7(A, B and C). Both of the unequal sandwiches demonstrate high sensitivity, comparable with the sensitivity of the conventional assay and could be used for precise detection of BNP and proBNP immunoreactivity in human blood.

The invention claimed is:

1. An immunoassay method for determining if a patient has heart failure, comprising the steps of:
   a) contacting a blood sample from the patient with a first antibody, or binding fragment thereof, specific for a region of a ring structure of BNP and proBNP, the region consisting of the amino acid sequence FGRKMDRISSSS (SEQ ID NO:3) or to a portion of this region, to obtain a first order immune complex;
   b) contacting the first order immune complex with a second antibody, or binding fragment thereof, to obtain a second order immune complex,
      wherein the second antibody, or binding fragment thereof, is specific for an epitope located on the first order immune complex, the epitope forming when the first antibody, or binding fragment thereof, binds BNP, proBNP, or a fragment thereof consisting of SEQ ID NO:3 or a portion thereof,
      the second antibody, or binding fragment thereof, not recognizing free BNP, free proBNP, or a free fragment thereof, or free first antibody, or which recognizes them with 10-fold or less affinity than it recognizes the first order immune complex, the second antibody being AB-BNP2, Ab-BNP4, or a binding fragment thereof; and
   c) determining if the patient has heart failure by detecting a concentration of the second order immune complex in the sample,
   an increased concentration of the second order immune complex relative to that in a healthy subject being indicative of an increased concentration of BNP and/or proBNP in the sample and that the patient has heart failure.

2. The method of claim 1, wherein in step a), a plasma sample from the patient is contacted with the first antibody.

3. The method of claim 1, wherein the first antibody is 24C5 monoclonal antibody.

4. A method for detecting BNP and/or proBNP in a sample, comprising the steps of:
   a) contacting the sample with a first antibody, or binding fragment thereof, specific for a region of a ring structure of BNP and proBNP, the region consisting of the amino acid sequence SEQ ID NO:3, or to a portion of this region, to obtain a first order immune complex;
   b) contacting the first order immune complex with a second antibody, or binding fragment thereof, to obtain a second order immune complex,
      wherein the second antibody, or binding fragment thereof, is specific for an epitope located on the first order immune complex, the epitope forming when the first antibody, or binding fragment thereof, binds BNP, proBNP, and a fragment thereof consisting of SEQ ID NO:3,
      the second antibody, or binding fragment thereof, not recognizing free BNP, free proBNP, or a free fragment thereof, or free first antibody, or which recognizes them with 10-fold or less affinity than it recognizes the first order immune complex, the second antibody being AB-BNP2, Ab-BNP4 or a binding fragment thereof; and
   c) detecting the presence of the second order immune complex,
   the presence of the second order immune complex being indicative of the presence of BNP and/or proBNP in the sample.

5. The method of claim 4, wherein the first antibody is the 24C5 monoclonal antibody.

6. The method of claim 4, wherein the sample is blood.

7. The method of claim 4, wherein the sample is plasma.

* * * * *

```
                        SEQUENCE LISTING

<160> NUMBER OF SEQ ID NOS: 3

<210> SEQ ID NO 1
<211> LENGTH: 32
<212> TYPE: PRT
<213> ORGANISM: Homo sapiens

<400> SEQUENCE: 1

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 2
<211> LENGTH: 108
<212> TYPE: PRT
<213> ORGANISM: Homo sapiens

<400> SEQUENCE: 2

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
            100                 105

<210> SEQ ID NO 3
<211> LENGTH: 12
<212> TYPE: PRT
```

```
<213> ORGANISM: Homo sapiens

<400> SEQUENCE: 3

Phe Gly Arg Lys Met Asp Arg Ile Ser Ser Ser Ser
1               5                   10
```